United States Patent
Popescu

(10) Patent No.: US 7,634,045 B2
(45) Date of Patent: Dec. 15, 2009

(54) FIFTH GENERATION X-RAY COMPUTED TOMOGRAPHY SYSTEM AND OPERATING METHOD

(75) Inventor: Stefan Popescu, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/184,406

(22) Filed: Aug. 1, 2008

(65) Prior Publication Data

US 2009/0034678 A1    Feb. 5, 2009

(30) Foreign Application Priority Data

Aug. 1, 2007    (DE) .................. 10 2007 036 038

(51) Int. Cl.
*A61B 6/00*    (2006.01)
(52) U.S. Cl. .................................. 378/10; 378/4
(58) Field of Classification Search .............. 378/4, 378/9, 10, 19, 62
See application file for complete search history.

(56) References Cited

U.S. PATENT DOCUMENTS

| | | | |
|---|---|---|---|
| 4,158,142 A | 6/1979 | Haimson | |
| 4,352,021 A | 9/1982 | Boyd et al. | |
| 4,521,900 A | 6/1985 | Rand | |
| 4,521,901 A | 6/1985 | Rand | |
| 4,606,061 A | 8/1986 | Ramamurti | |
| 5,125,012 A * | 6/1992 | Schittenhelm | 378/10 |
| 5,191,600 A | 3/1993 | Vincent et al. | |
| 5,197,088 A * | 3/1993 | Vincent et al. | 378/10 |
| 5,305,363 A * | 4/1994 | Burke et al. | 378/4 |
| 6,907,110 B2 * | 6/2005 | Apel et al. | 378/143 |
| 2006/0159221 A1 | 7/2006 | Popescu | |

FOREIGN PATENT DOCUMENTS

| | | |
|---|---|---|
| DE | 40 15 180 C2 | 11/1991 |
| DE | 40 15 105 C3 | 12/1991 |
| DE | 10 2004 061 347 B3 | 9/2006 |

\* cited by examiner

*Primary Examiner*—Irakli Kiknadze
(74) *Attorney, Agent, or Firm*—Schiff Hardin LLP

(57) ABSTRACT

A fifth generation x-ray computed tomography system has at least one electron beam generator that generates at least one electron beam, an anode ring or partial anode ring arranged concentrically around a system axis, from which x-ray radiation can be generated at a number of focus positions by striking the ring or partial ring with the at least one electron beam, a detector ring or partial detector ring arranged concentrically around the system axis, with a number of detector elements forming at least one detector row to detect the impinging x-ray radiation; and a rotatable support frame on which filter and collimator elements are carried. The filter and collimator elements are arranged at the focus on the support frame at at least two positions that are angularly offset relative to one another.

17 Claims, 4 Drawing Sheets

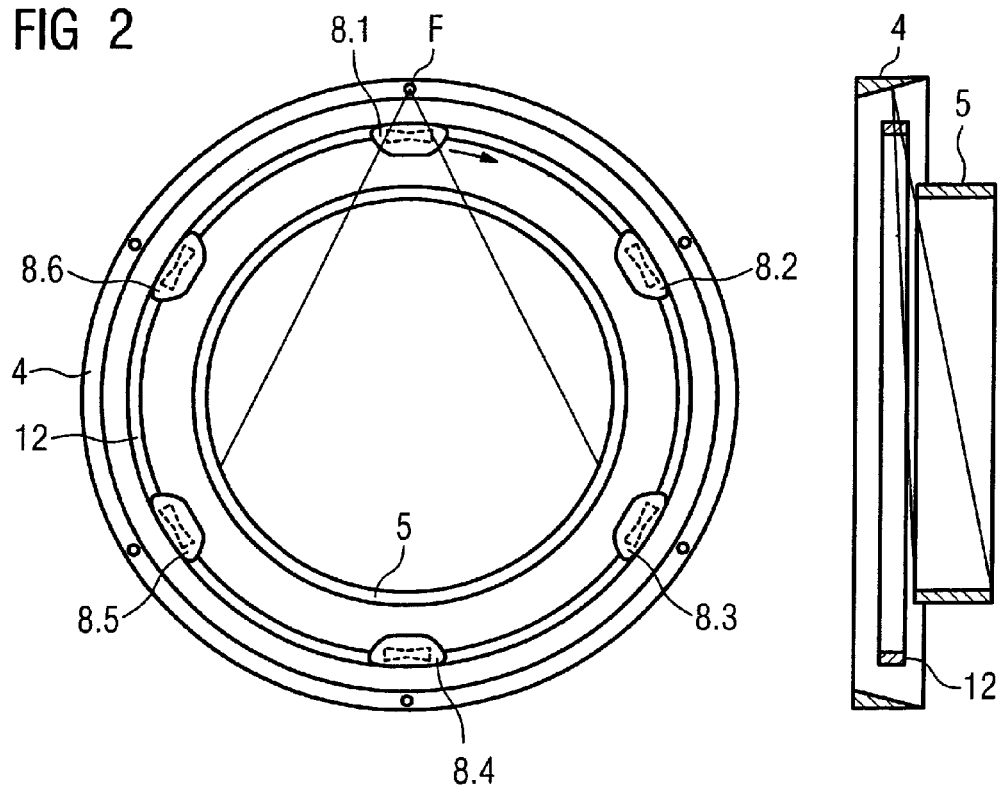
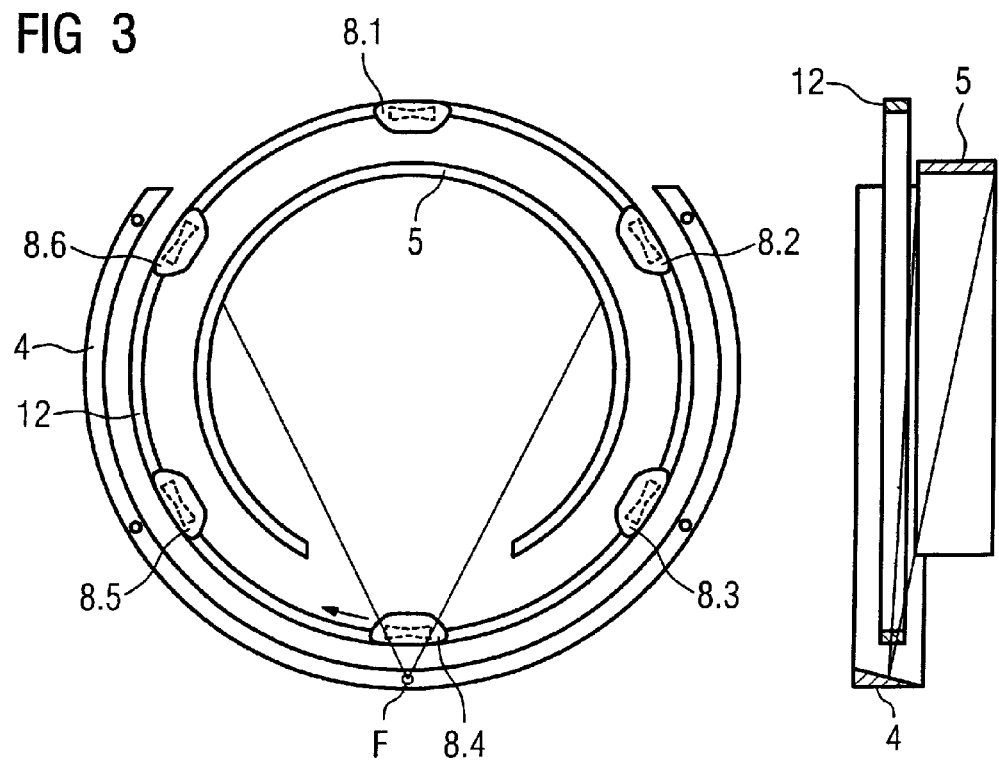

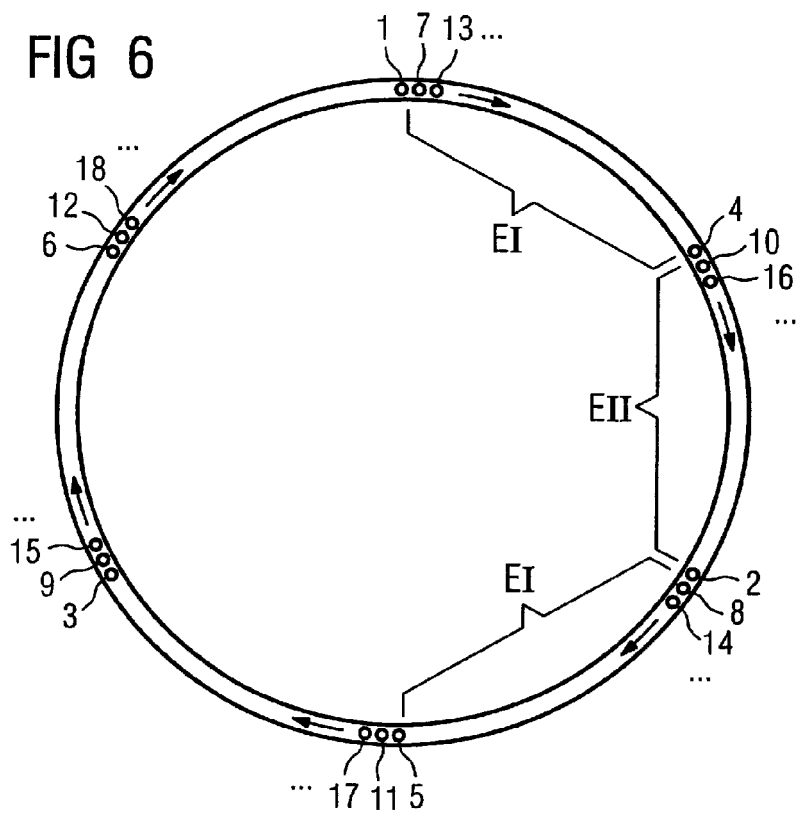
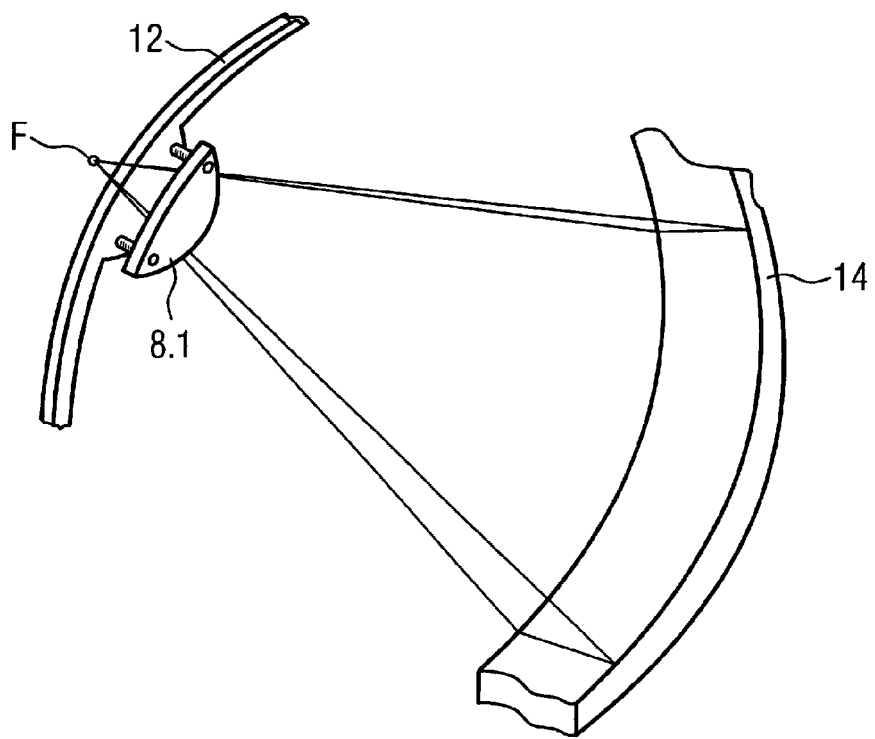

FIFTH GENERATION X-RAY COMPUTED TOMOGRAPHY SYSTEM AND OPERATING METHOD

BACKGROUND OF THE INVENTION

1. Field of the Invention

The present invention concerns a fifth generation x-ray computed tomography (CT) system of the type having at least one electron beam generator that generates at least one electron beam, an anode ring or partial anode ring arranged concentrically around a system axis, from which x-ray radiation is generated at a number of focus positions by striking said anode ring or partial anode ring with at least one electron beam, a detector ring or partial detector ring arranged concentrically around the system axis, with a number of detector elements forming at least one detector line to detect the impinging x-ray radiation; and a rotatable support frame to accommodate filter and collimator elements. The invention also concerns a method to control such an x-ray computed tomography system.

2. Description of the Prior Art

Fifth generation CT systems are generally known. These are CT systems with a stationary, annular anode which is arranged around the system axis, wherein x-ray radiation is generated (emitted) at a number of positions on the stationary anode in various ways. Such a CT also has a (likewise stationary) annular detector. Rotating parts are hereby largely foregone, so a relatively high scan rate can be achieved. For example, an electron emitter with corresponding deflection and concentration devices is used to generate x-ray radiation, with which devices an electron beam can be directed at desired positions of the anode ring where x-ray radiation is emitted from a focus created at those positions. U.S. Pat. Nos. 4,158,142; 4,352,021; 4,521,900 and 4,521,901 disclose examples of such "electron beam" CT systems.

Other known variants of the fifth generation CT systems use a laser in order to excite electron emission at an arbitrary point on a cathode ring arranged opposite the anode ring. The emitted electrons generate x-ray radiation on the opposite anode at the focus arising there. The document U.S. Pat. No. 4,606,061 discloses such an embodiment.

A CT system with stationary anode ring and stationary detector ring is known from DE 40 15 105 C3 and DE 40 15 180, in which a cathode ring is divided into a number of segments that can be individually activated. By activating the individual cathode segments, x-ray sources distributed along the circumference of the anode ring can be activated in a targeted manner, with which x-ray sources a circular scan of a patient is enabled.

These known CT systems have the advantage that neither an x-ray tube nor a detector (as it is typical in the third generation CT systems) must be rotated at high speed on a gantry around a system axis, so many problems are avoided that arise due to the high centrifugal forces that occur, as well as due to the necessity to transmit high voltages, high currents and large data sets via slip rings. Due to the very quickly adjustable focus, however, new problems occur with regard to optical beam filtering and collimation as well as with regard to optimal scatter radiation suppression at the detector. Optimal filtering, collimation and scatter radiation suppression requires filters and collimators that are essentially fashioned symmetrical to an imaginary axis (Focus-System Axis), and thus are designed to be variable relative to the circumferential direction. Simple filters that have a rotationally symmetrical design over the entire extent are less suitable.

One possibility for better radiation filtering and collimation of the x-ray radiation is described in DE 10 2004 061 347 B3. This document discloses a fifth generation CT system in which a focus-side filter (including a bowtie filter) and a detector-side collimator are mounted on a rotating ring, wherein both the filter and the opposite collimator are rotated such that they are respectively positioned at the focus position (here activated by a laser).

This embodiment of a CT system has the disadvantage exists that the running speed of the focus must correspond to the rotation speed of the support frame on which the focus-side filter and the detector-side collimator are mounted. The possibilities of this CT with regard to variable focus positioning are therefore severely limited, and the revolution speed of the focus is also limited by the maximum rotation speed of the support frame.

SUMMARY OF THE INVENTION

An object of the invention to provide a fifth generation CT system, and an operating method therefor, that have the advantages of not using a rotating x-ray tube and a rotating x-ray detector, but that allows an optimal focus-side filtering and collimation, and possibly detector-side collimation, with the variability with regard to the quickly changing positioning of the focus being retained.

The invention is based on the insight that, with the use of multiple filters and collimator elements mounted on a rotating support frame, it is possible to filter the x-ray radiation arising at different focus positions corresponding to the filtering that is typical in third generation CT systems, and therefore to achieve a corresponding high image quality given simultaneous optimal dose utilization. Since the rotation speed of the support frame is additionally reduced corresponding to the number of the provided positions for filters and collimator elements, the arising g-force load of this support frame is also correspondingly reduced. For example, if a support frame is considered with a typical diameter of 1 m and a rotation speed of 10 revolutions per sec (which corresponds to the typical rotation speed of the focus in a fifth generation scanner), g-forces in the range of 2000 g arise, while a use of such a support frame with six positions in total for focus-side filters or collimator elements reduces these g-forces to 80 g. The design expenditure for such a support frame can be significantly reduced relative to the prior art (according to the previously cited DE 10 2004 061 347 B3), due to this drastic reduction of the occurring g-forces. It is also no longer necessary to continuously move the focus in a circle; rather, the possibility exists to have the focus jump among the individual positions of the filter elements, to the thermal loads of the anode are reduced (or at least are better distributed) significantly relative to the prior art.

Different jump patterns for the focus are possible in this embodiment. For example, the focus can successively occupy filter positions on the anode ring (located on the support frame) in a sequence. An additional small offset of the focus in the circumferential direction is implemented after each sequence completion so that the anode ring is scanned in as many segments as that are positions for the focus-side filters and collimator elements. Another alternative is for respectively opposite positions are to be occupied in sequence, and after the complete processing of two opposite positions, the next two positions (angularly offset from the preceding two) of the filter elements are activated. A complete, circular scanning of the anode ring or partial anode ring is also possible in this manner.

Accordingly, a fifth generation x-ray computed tomography system in accordance with the invention has at least one electron beam generator that generates at least one electron beam, an anode ring or partial anode ring arranged concentrically around a system axis, from which x-ray radiation is generated at a number of focus positions by striking the ring or partial ring with at least one electron beam, a detector ring or partial detector ring arranged concentrically around the system axis, with a number of detector elements forming at least one detector row to detect the x-ray radiation incident thereon, and a rotatable support frame on which filter and collimator elements.

According to the invention, the filter and collimator elements are attached at the focus at at least two positions that are angularly offset from one another on the support frame.

With this embodiment it is possible to activate different alternating angle positions at which the filters and collimator elements are located on the anode ring, and each focus that arises on the anode ring has an optimally fashioned filter that is also variable in the $\phi$-direction. The same also applies for the collimator that is used. If a stationary filter or collimator were to be used, no variation in the $\phi$-direction would be possible. The filter and collimator design thus corresponds to an individual filter or collimator installed on an x-ray tube that rotates on a gantry. Since the rotation speed is functionally reduced, corresponding to the number of the positions at which filter elements are mounted on the support frame, the g-forces are also reduced (as shown previously). The design expenditure for the structure of such support frames is hereby significantly reduced, such that overall a more economical structure of such x-ray computed tomography systems is made possible.

According to the invention, the angularly offset positions of the focus-side filter elements and collimator elements can be located at identical angle intervals on the support frame. For example, the angle intervals of 180° are suitable given the use of only two sets of filters or collimator elements, or 120° given three sets, or 90° given four sets, or 60° given six sets of filters and collimator elements. In principle, more than six sets of filters and collimator elements can be used; a good compromise with regard to the design expenditure and the effectiveness appears to be achieved when four to six sets are used.

A bowtie filter, spectral filter, z-collimators or $\phi$-collimators that can also be combined into a single component according to the invention can be used as focus-side filters, for example.

The x-ray computed tomography system described herein typically has a stationary detector ring that surrounds the system axis in a closed manner. It is possible, however, to fashion this stationary detector ring as a partial detector ring that only partially surrounds the system axis.

In this embodiment, it is advantageous for the detector ring to encompass at least one angle range of 180°, advantageously in addition to the fan angle used for the x-ray radiation. Naturally, such a detector ring can be fashioned with a single line and multiple lines.

Both a completely revolving anode ring and even a partial anode ring that does not entirely surround the system axis can be used with regard to the embodiment of the stationary anode ring.

Identically designed filter elements can be provided on the support frame, but it is also possible to simultaneously use differently designed filter elements on the support frame, the filter elements being adapted (for example) corresponding to a different design of fan angles or to accommodate a different generated radiation energy. This means that multiple different filter elements can thus be used on a single support frame, such that different fan angles are formed at different support frame positions with the aid of these filter elements. For example, these different fan angles can be used in alternation during a single examination, or the possibility exists to switch between the individual fan angles. The same also correspondingly applies for filters of different design that take into account different x-ray energies.

In principle, such different filter sets can be permanently mounted on the support frame. However, it is also possible to provide the support frame with adapter elements which are suitable for connection of different filter elements. Either filter elements can be manually exchanged between individual examinations in this embodiment, or it is possible to integrate an automatically operating exchange device into a CT system. Such an exchange device automatically implements the exchange of the individual filter elements on the support frame between the examinations. This can be a robot-like device that provides the support frame with the same or different filter sets corresponding to a selection made by an operator. Naturally, the operating mode of the CT system must be appropriately selected (corresponding to the selected filter sets) in order to generate the correct x-ray energy at the filter positions, as well as to make the correct associations of the measured detector values corresponding to the data acquisition. For example, tomographical data sets that originate from three different or multiple different x-ray energies can be generated in a very simple manner during a single examination with the use of, for example, three different filter sets. Such an x-ray CT system is significantly more variable compared to the known CT systems that are relatively inflexible with regard to their filter equipment and the possible usable energies.

Moreover, the support frame can have at least two detector-side collimators arranged at an angular offset between each other, the collimators respectively detecting the respective beam fan of the opposite focus, with each collimator position being associated with an opposite filter position.

Corresponding to the system in accordance with the invention described above, the above object is achieved by a method to control a fifth generation x-ray computed tomography system having an electron beam generator for generation of at least one electron beam, an anode ring or partial anode ring arranged concentrically around a system axis, from which anode ring or partial anode ring x-ray radiation is generated in succession from a number of focus positions; and a detector ring or partial detector ring arranged concentrically around the system axis, the detector ring or partial detector ring detecting the x-ray radiation emanating from the respective foci, wherein according to the invention at least two focus-side sets of filter and collimator elements arranged angularly offset relative to one another are rotated with a rotatable support frame, and the focus positions are activated by the electron beam, such that one of the at least two sets of filter and collimator elements is located in alternation at each activated focus position.

In this method, different activation variants and activation sequences can be enabled dependent on the design and number of the different filter sets and the employed radiation energies or different employed radiation fans, such that tomographical data sets and therefore also tomographical reconstructions of various specifications are possible.

BRIEF DESCRIPTION OF THE DRAWINGS

FIG. 2 shows transversal and longitudinal sections through a schematic representation of an x-ray computed tomography system in the region of the support frame with a complete detector ring and anode ring.

FIG. 3 shows transverse and longitudinal sections through a schematic representation of an x-ray computed tomography system in the region of the support frame with a partially revolving detector ring and anode ring.

FIG. 6 illustrates an alternate activation sequence of the focus positions with two different electron energies.

FIG. 7 shows a portion of a support frame with filter set and opposing, likewise rotating detector-side collimator.

DESCRIPTION OF THE PREFERRED EMBODIMENTS

Figure 1:
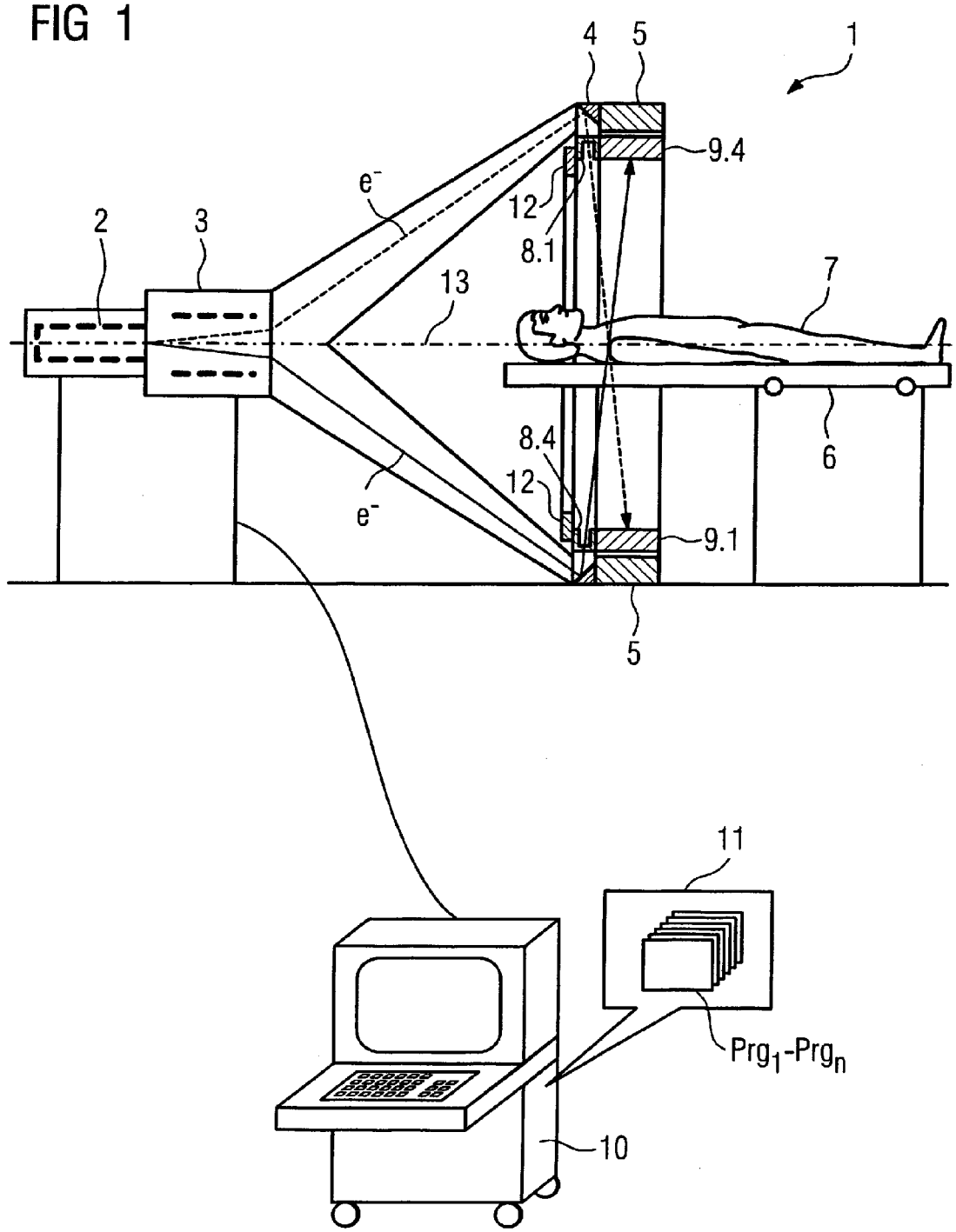
FIG. 1 illustrates a fifth generation x-ray computed tomography system according to the invention.

In the following the invention is described in detail using preferred exemplary embodiments with the aid of figures, wherein only the features necessary for comprehension of the invention are shown. The following reference characters are used: 1: fifth generation x-ray computed tomography system; 2: electron beam emitter; 3: deflection system; 4: stationary anode ring; 5: stationary detector ring; 6: displaceable patient bed; 7: patient; 8.1 through 8.6: filter sets on support frame; 8.1.1: bowtie filter; 8.1.2, 8.1.3: phi-filter; 9.1, 9.4: detector-side collimators/scatter radiation filters; 10: control and computer system; 11: memory space in the computer system; 12: rotatable support frame; 13: system axis; 14: scattered radiation filter; I, II: sectors of the stationary anode ring; EI, EII: anode ring sectors with different x-ray energies; F: focus; e–: electrons; γ: x-ray radiation; φ: fan angle; z: z-axis.

FIG. 1 shows an exemplary fifth generation x-ray computed tomography system 1 according to the invention, with an electron beam generator 2 that accelerates an electron beam e– in a targeted and focused manner by a deflection system 3 onto a number of individually activatable focus points on a stationary anode ring 4. In this example this stationary anode ring 4 extends 360° around the system axis 13 in a closed manner so that x-ray radiation can be generated at any point on the anode ring 4 (and thus in an arbitrary angle position on the anode ring 4). Furthermore, a detector ring 5 encompassing 360° is shown with which the generated γ-radiation can be detected after passage through the body of a patient 7.

The patient 7 is located on a patient bed 6 movable in the direction of the system axis 13 and is successively (for a sequential scan) or continuously (for a spiral scan) moved through the measurement field of the CT during a scan.

According to the invention, the CT 1 has a rotating support frame 12 in the region of the radiation generation and in the measurement region, which support frame 12 respectively possesses a focus-side filter set 8.1 and 8.4 at multiple (here six) positions. In the shown example, six detector-side scattered radiation filters or, respectively, collimators 9.1 and 9.4 are additionally arranged on the support frame 12.

For a scan, all positions of the filter sets distributed over the extent of the support frame can now be controlled at very small time intervals with the aid of the controllable electron beam e–. The rotation speed of the support frame 12 can be reduced, and it is possible to adapt the activation positions to a desired scan pattern.

Furthermore, a control and computer system 10 is provided that executes the control of the support frame, the electron beam and of the patient bed and receives detector data. Image reconstructions from the acquired detector data also can be implemented with this control and computer system 10.

The illustrated embodiment of an EBCT system is an example. In principle, the embodiment of the filter and collimator arrangement according to the invention on a support frame can be used in connection with all fifth generation CT systems without departing from the scope of the invention.

FIG. 2 shows further sections of a CT system according to the invention in the region of anode ring 4, support frame 12 and detector ring 5. The left side shows the support frame 12 on which six filter sets 8.1 through 8.6. The filter sets 8.1 through 8.6 exhibit the same intervals from one another and each include a bowtie filter (shown in dashes) and a z-filter and phi-filter. The anode ring 4, on which the active focus F is shown in the "12 o'clock" position is concentric to this support frame 12. A radiation beam emanates from this focus F, which is treated with the use of the filter set 8.1 (similar to focus-side filters known from 3rd generation CT systems). In operation, the positions of the filter sets 8.1 through 8.6 are activated in a sequence in specific jump patterns with the deflection device of the electron beam, such that a respective filter exists at the point of each arising active focus, and therefore the x-ray radiation emitted from that focus can be filtered in a desired manner even in the φ-direction (as is indicated by the bowtie filter), and in this manner leads to a better dose utilization.

The same system composed of an anode ring, support frame and detector ring is shown again in longitudinal section on the right side of FIG. 2.

A different (relative to FIG. 2) embodiment variant of the CT system according to the invention in the scan region is shown in FIG. 3. This embodiment has an anode ring 4 that is not closed, and that is open at the top over a range of approximately 90°. Opposite the anode ring is a detector ring 5 that has an opening on the opposite side. A closed support frame 12 is located between the anode ring 4 and the detector ring 5, on which filter sets 8.1 through 8.6 are attached with uniform distribution at six positions on the circumference.

In principle the functioning of such a CT with open anode ring and open detector ring is similar to the functioning with closed anode ring and detector ring; only the scanning is partially limited.

Figure 4:
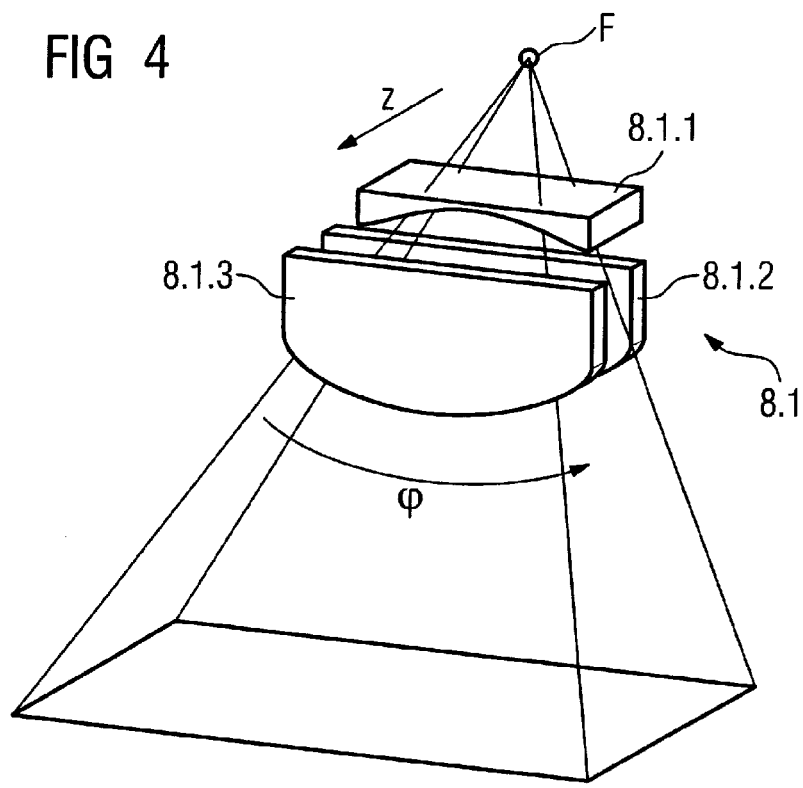
FIG. 4: is a schematic representation of a filter set.

The design of a filter set 8.1 is schematically depicted in FIG. 4. FIG. 4 shows this filter set 8.1 in the position of an active focus F that generates a radiation beam. This radiation beam travels through a bowtie filter 8.1.1 and is limited by the collimators 8.1.2 and 8.1.3 in the z-direction and shaped in the φ-direction.

Figure 5:
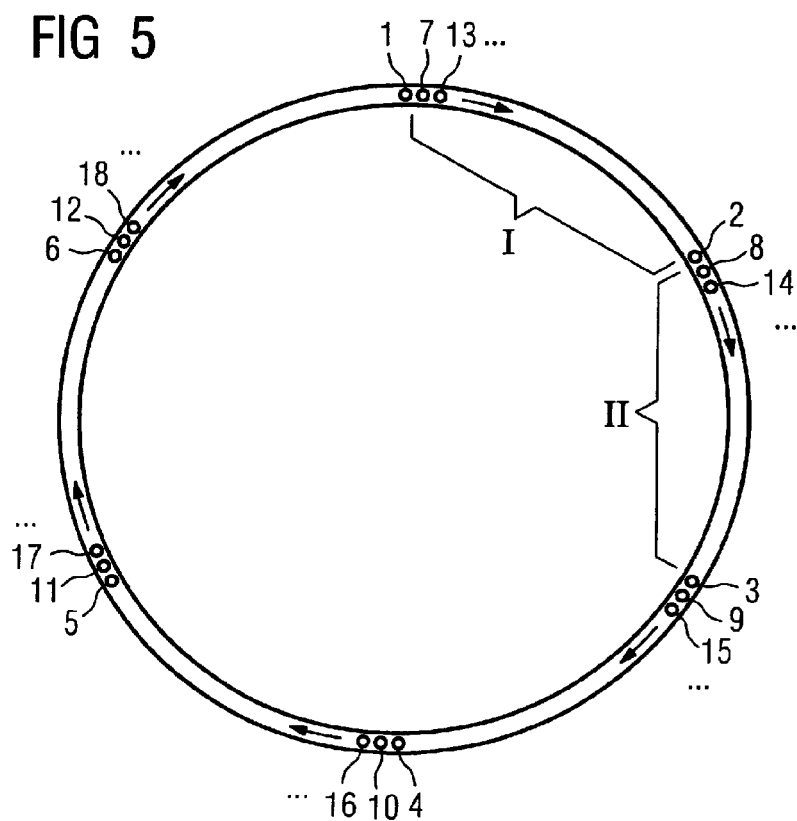
FIG. 5 illustrates an exemplary activation sequence of the foci.

Two exemplary activation patterns for the jump pattern for the arising foci are show in FIGS. 5 and 6. FIG. 5 shows a variant of a jump pattern in which a support frame (corresponding to FIG. 2) is used with six filter sets uniformly distributed on the periphery. For example, the uppermost position 1 can be activated first, then the nearest position 2 of the second filter set in the circumferential direction in the clockwise direction [sic], followed by the position 3 of the third filter set, etc., until all filter sets located on the periphery have been activated, whereupon a rotation of the support frame in the meanwhile would lead to a small offset in the clockwise direction in the "12 o'clock position", and therefore a next position 7 is activated (corresponding to the distance traveled by the support frame 12 in the meanwhile), and so on. This is implemented until the support frame has traveled a sixth of the circumference, whereupon the process starts again from the beginning while a new filter set is positioned at the "12 o'clock" position.

The segments I and II shown here indicate the path of a filter set during a complete 360° scan.

Although a single electron or x-ray energy is used in the activation series shown in FIG. 4, for example, it is more advantageous to employ a different pattern (as is shown, for example, in FIG. 6) for the use of two different electron energies.

FIG. 6 shows this altered activation order. Here the position 1 in the "12 o'clock" position is initially activated with a first energy EI; omitting the next filter set, an activation of the filter set after next in the position 2 shown here then follows, followed by an omission of the third filter set with an activation of position 3 at the fifth filter set. These positions 1, 2, 3 are activated with an identical electron energy, or identical x-ray energy; after this a second electron energy EII or x-ray energy arising therefrom be generated, or even a second electron beam with different x-ray energy can be used and the positions 4, 5 and 6 can now be activated with this electron beam. Exemplary filter sets are then located at positions 4, 5 and 6 which differ from the filter sets at positions 1, 2 and 3 due to the different employed x-ray energy, such that overall an optimally adapted filter exists for each x-ray energy. Naturally, other jump patterns are also possible corresponding to the jump pattern shown here, possibly with a higher or lower number of activation positions (corresponding to the number of employed filter sets).

As described above, such filter sets can be automatically exchanged so that a fast adaptation of the CT to the desired scan conditions is possible.

A support frame 12 on which is located a filter set 8.1 is additionally presented again in part in FIG. 7, wherein a scattered radiation filter 14 is shown opposite said filter set 8.1, which scattered radiation filter 14 moves along with the rotating support frame 12 and respectively implements an optimal scattered radiation filtering (possibly adapted to the focus-side filter set).

It is understood that the features of the invention cited in the preceding can be used not only in the respective specified combination but also in other combinations or alone without departing from the scope of the invention.

In summary of a fifth generation CT system in accordance with the invention achieves a significantly improved and more flexibly usable filter system, such that higher scan speeds are possible without loss of image quality and a more flexible usage possibility is enabled with regard to the simultaneous scanning of different x-ray energies.

Although modifications and changes may be suggested by those skilled in the art, it is the intention of the inventor to embody within the patent warranted hereon all changes and modifications as reasonably and properly come within the scope of his contribution to the art.

I claim as my invention:

1. A fifth generation x-ray computed tomography system comprising:
    a stationary anode ring selected from the group consisting of a complete anode ring proceeding concentrically around a system axis and a partial anode ring extending concentrically around the system axis;
    an electron beam generator that generates at least one electron beam that strikes said anode ring successively at a number of focused positions to cause x-ray radiation to be emitted at each of said focus positions;
    a stationary detector ring selected from the group consisting of a complete detector ring extending concentrically around the system axis and a partial detector ring extending concentrically around the system axis, comprising a number of detector elements forming at least one detector row to detect said x-ray radiation;
    a rotatable support frame mounted for rotation around said system axis; and
    at least two sets of x-ray radiation-influencing components, selected from the group consisting of x-ray filters and a beam collimator, said number of sets of x-ray radiation-influencing components being mounted on said support frame at respective positions on said support frame with an angular offset therebetween, adjacent to said focus positions, said support frame being rotatable to position said number of sets of x-ray radiation-influencing components relative to said focus positions to cause said number of sets of x-ray radiation-influencing components to interact with and modify said x-ray radiation between said focus positions and said detector ring.

2. An x-ray computed tomography system as claimed in claim 1 wherein said number of sets of x-ray radiation-influencing components are mounted on said support frame with equal angular offsets respectively therebetween.

3. An x-ray computed tomography system as claimed in claim 2 wherein said angular offsets are selected from the group consisting of 180°, 120°, 90° and 60°.

4. An x-ray computed tomography system as claimed in claim 1 wherein each of said sets of x-ray radiation-influencing components comprises a bowtie filter.

5. An x-ray computed tomography system as claimed in claim 1 wherein each of said sets of x-ray radiation-influencing components comprises a spectral filter.

6. An x-ray computed tomography system as claimed in claim 1 wherein each of said sets of x-ray radiation-influencing components comprises a z-collimator.

7. An x-ray computed tomography system as claimed in claim 1 wherein each of said sets of x-ray radiation-influencing components comprises a φ-collimator.

8. An x-ray computed tomography system as claimed in claim 1 wherein each of said sets of x-ray radiation-influencing components comprises a unitary component consisting of two x-ray filters and a collimator.

9. An x-ray computed tomography system as claimed in claim 1 wherein at least two of said number of sets of x-ray radiation-influencing components each comprise a filter, with the respective filters having a different filtering effect on said x-ray radiation.

10. An x-ray computed tomography system as claimed in claim 1 wherein each of said number of sets of x-ray radiation-influencing components comprises a number of filters, and an adapter configured to receive and hold one of said filters at a time in a position to interact with said x-ray radiation.

11. An x-ray computed tomography system as claimed in claim 10 wherein each of said number of sets of x-ray radiation-influencing components comprises an automatic exchange device configured to non-manually exchange respective filters, from among said number of filters, in said adapter.

12. An x-ray computed tomography system as claimed in claim 1 wherein said detector ring comprises a scatter radiation filter disposed adjacent said detector elements.

13. An x-ray computed tomography system as claimed in claim 1 wherein at least two of said sets of x-ray radiation-influencing components comprise a filter and a detector-side collimator located opposite each other on said support frame.

14. An x-ray computed tomography system as claimed in claim 1 wherein said at least one electron beam generator is an electron beam emitter comprising electron beam-influencing components for targeted deflection and concentration of said at least one electron beam.

15. An x-ray computed tomography system as claimed in claim 1 wherein said electron beam generator comprises a laser that emits a laser beam onto a cathode to cause electron emission from said cathode to generate said at least one electron beam.

16. An x-ray computed tomography system as claimed in claim 1 wherein said at least one electron beam generator comprises an annular multi-emitter cathode, selected from the group consisting of an annular multi-emitter cathode that completely surrounds said system axis and a partially annular multi-emitter cathode that partially surrounds said system axis, said multi-emitter cathode comprising a number of individually activatable segments that each, upon activation thereof, emits electrons to form said at least one electron beam.

17. A method for operating a fifth generation x-ray computed tomography system comprising a stationary anode ring selected from the group consisting of a complete anode ring proceeding concentrically around a system axis and a partial anode ring extending concentrically around the system axis, an electron beam generator that generates at least one electron beam that strikes said anode ring successively at a number of focused positions to cause x-ray radiation to be emitted at each of said focus positions, a stationary detector ring selected from the group consisting of a complete detector ring extending concentrically around the system axis and a partial detector ring extending concentrically around the system axis, comprising a number of detector elements forming at least one detector row to detect said x-ray radiation, and a rotatable support frame mounted for rotation around said system axis, said method comprising the steps of:

mounting at least two sets of x-ray radiation-influencing components, selected from the group consisting of x-ray filters and a beam collimator, on said support frame at respective positions on said support frame with an angular offset therebetween, adjacent to said focus positions; and rotating said support frame to position said number of sets of x-ray radiation-influencing components relative to said focus positions to cause said number of sets of x-ray radiation-influencing components to interact with and modify said x-ray radiation between said focus positions and said detector ring.

\* \* \* \* \*